(12) United States Patent
Yanai et al.

(10) Patent No.: US 9,371,826 B2
(45) Date of Patent: Jun. 21, 2016

(54) IMPELLER POSITION COMPENSATION USING FIELD ORIENTED CONTROL

(71) Applicant: THORATEC CORPORATION, Pleasanton, CA (US)

(72) Inventors: Masamichi Yanai, Ann Arbor, MI (US); Jeffrey H. Campau, Pinckney, MI (US); Jason C. Nanna, Plymouth, MI (US)

(73) Assignee: THORATEC CORPORATION, Pleasanton, CA (US)

( * ) Notice: Subject to any disclaimer, the term of this patent is extended or adjusted under 35 U.S.C. 154(b) by 226 days.

(21) Appl. No.: 13/748,780

(22) Filed: Jan. 24, 2013

(65) Prior Publication Data
US 2014/0205467 A1 Jul. 24, 2014

(51) Int. Cl.
*F04B 35/04* (2006.01)
*H02P 6/18* (2006.01)
(Continued)

(52) U.S. Cl.
CPC .............. *F04B 35/04* (2013.01); *A61M 1/1015* (2014.02); *A61M 1/122* (2014.02); *F04D 13/024* (2013.01); *F04D 15/0088* (2013.01);
(Continued)

(58) Field of Classification Search
CPC .............. F04D 29/048; F04D 29/0473; F04D 15/0066; F04D 13/024; F04D 29/428; F04D 15/0088; A61M 5/142; A61M 5/14236; A61M 5/16831; A61M 5/172; A61M 2005/14208; A61M 1/122; A61M 1/1015; F04B 35/04; H02P 6/18
USPC ........................ 623/3.13, 3.14, 3.28; 604/4.01
See application file for complete search history.

(56) References Cited

U.S. PATENT DOCUMENTS 1,093,868 A 4/1914 Leighty
2,684,035 A 7/1954 Kemp
(Continued)

FOREIGN PATENT DOCUMENTS

CN 102239334 A 11/2011
CN 102341600 A 2/2012
(Continued)

OTHER PUBLICATIONS

International Search Report and Written Opinion of PCT/US2014/012448 mailed on Feb. 19, 2014, 8 pages.
(Continued)

*Primary Examiner* — Justin Jonaitis
*Assistant Examiner* — Christopher Brunjes
(74) *Attorney, Agent, or Firm* — Kilpatrick Townsend & Stockton LLP

(57) ABSTRACT

A centrifugal pump system having an impeller rotating with first and second magnetic structures on opposite surfaces. A levitation magnetic structure is disposed at a first end of a pump housing having a levitating magnetic field for axially attracting the first magnetic structure. A multiphase magnetic stator at a second end of the pump housing generates a rotating magnetic field for axially and rotationally attracting the second magnetic structure. A commutator circuit provides a plurality of phase voltages to the stator. A sensing circuit determines respective phase currents. A controller calculates successive commanded values for the phase voltages in response to the determined phase currents and a variable commutation angle. The angle is selected to correspond to an axial attractive force of the stator that maintains a levitation of the impeller at a centered position within the pumping chamber.

6 Claims, 4 Drawing Sheets

(51) Int. Cl.

| | | |
|---|---|---|
| *F04D 13/02* | (2006.01) | |
| *F04D 29/048* | (2006.01) | |
| *F04D 29/42* | (2006.01) | |
| *F04D 29/047* | (2006.01) | |
| *F04D 15/00* | (2006.01) | |
| *A61M 1/12* | (2006.01) | |
| *A61M 1/10* | (2006.01) | |

(52) U.S. Cl.
CPC ......... *F04D 29/048* (2013.01); *F04D 29/0473* (2013.01); *F04D 29/428* (2013.01); *H02P 6/18* (2013.01)

(56) References Cited

U.S. PATENT DOCUMENTS

| | | |
|---|---|---|
| 3,510,229 A | 5/1970 | Smith |
| 3,932,069 A | 1/1976 | Giardini et al. |
| 3,960,468 A | 6/1976 | Boorse et al. |
| 4,149,535 A | 4/1979 | Volder |
| 4,382,199 A | 5/1983 | Isaacson |
| 4,392,836 A | 7/1983 | Sugawara |
| 4,507,048 A | 3/1985 | Belenger et al. |
| 4,540,402 A | 9/1985 | Aigner |
| 4,549,860 A | 10/1985 | Yakich |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papantonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,969,865 A | 11/1990 | Hwang et al. |
| 4,985,014 A | 1/1991 | Orejola |
| 4,995,857 A | 2/1991 | Arnold |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,275,580 A | 1/1994 | Yamazaki |
| 5,290,227 A | 3/1994 | Pasque |
| 5,290,236 A | 3/1994 | Mathewson |
| 5,306,295 A | 4/1994 | Kolff et al. |
| 5,312,341 A | 5/1994 | Turi |
| 5,332,374 A | 7/1994 | Kricker et al. |
| 5,346,458 A | 9/1994 | Affeld |
| 5,354,331 A | 10/1994 | Schachar |
| 5,360,445 A | 11/1994 | Goldowsky |
| 5,370,509 A | 12/1994 | Golding et al. |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,533,957 A | 7/1996 | Aldea |
| 5,569,111 A | 10/1996 | Cho et al. |
| 5,575,630 A | 11/1996 | Nakazawa et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Izraelev |
| 5,941,813 A | 8/1999 | Sievers et al. |
| 5,947,703 A | 9/1999 | Nojiri et al. |
| 5,951,263 A | 9/1999 | Taylor et al. |
| 5,964,694 A | 10/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,190,304 B1 | 2/2001 | Downey et al. |
| 6,206,659 B1 | 3/2001 | Izraelev |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,264,635 B1 | 7/2001 | Wampler et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,351,048 B1 | 2/2002 | Schob et al. |
| 6,375,607 B1 | 4/2002 | Prem |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |

(56) References Cited

U.S. PATENT DOCUMENTS

| | | |
|---|---|---|
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,884,210 B2 | 4/2005 | Nose et al. |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,027,875 B2 | 4/2006 | Siess et al. |
| 7,048,681 B2 | 5/2006 | Tsubouchi et al. |
| 7,112,903 B1 | 9/2006 | Schob |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaegashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 2001/0039369 A1 | 11/2001 | Terentiev |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0008496 A1* | 1/2005 | Tsubouchi et al. .......... 417/44.2 |
| 2005/0089422 A1 | 4/2005 | Ozaki et al. |
| 2005/0141887 A1* | 6/2005 | Lelkes ............... H02P 6/085 388/813 |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2007/0078293 A1 | 4/2007 | Shambaugh, Jr. |
| 2007/0114961 A1* | 5/2007 | Schwarzkopf ......... H02P 6/085 318/400.01 |
| 2007/0134993 A1 | 6/2007 | Tamez et al. |
| 2007/0213690 A1 | 9/2007 | Phillips et al. |
| 2007/0231135 A1 | 10/2007 | Wampler et al. |
| 2007/0297923 A1 | 12/2007 | Tada |
| 2008/0021394 A1 | 1/2008 | LaRose et al. |
| 2008/0030895 A1 | 2/2008 | Obara et al. |
| 2008/0124231 A1 | 5/2008 | Yaegashi |
| 2009/0041595 A1* | 2/2009 | Garzaniti ............. A61M 1/101 417/356 |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2010/0185280 A1 | 7/2010 | Ayre et al. |
| 2010/0266423 A1* | 10/2010 | Gohean .................. F04B 17/04 417/53 |
| 2011/0118766 A1 | 5/2011 | Reichenbach et al. |
| 2011/0118829 A1 | 5/2011 | Hoarau et al. |
| 2011/0129373 A1 | 6/2011 | Mori |
| 2011/0243759 A1* | 10/2011 | Ozaki ................... A61M 1/101 417/279 |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | LaRose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 58/9535 | 1/1983 |
| JP | 04/091396 A | 3/1992 |
| JP | 04/148094 A | 5/1992 |
| JP | 05/021197 U | 3/1993 |
| JP | 06/014538 U | 2/1994 |
| JP | 2006/014538 U | 2/1994 |
| JP | 06/053790 U | 7/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |
| JP | 2004/209240 A | 7/2004 |
| JP | 2004/332566 A | 11/2004 |
| JP | 2004/346925 A | 12/2004 |
| JP | 2005/94955 | 4/2005 |
| JP | 2005/127222 A | 5/2005 |
| JP | 2005/270345 A | 10/2005 |
| JP | 2005/270415 A | 10/2005 |
| JP | 2005/287599 A | 10/2005 |
| JP | 2006/167173 A | 6/2006 |

(56) References Cited

FOREIGN PATENT DOCUMENTS

| | | |
|---|---|---|
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2006/254619 | 9/2009 |
| JP | 2010/136863 A | 6/2010 |
| WO | 93/07388 A1 | 4/1993 |
| WO | 96/31934 | 10/1996 |
| WO | 97/42413 A1 | 11/1997 |
| WO | 2005/028000 A1 | 3/2005 |
| WO | 2005/034312 A2 | 4/2005 |
| WO | 2010/067682 A1 | 6/2010 |
| WO | 2010/101082 A1 | 9/2010 |
| WO | 2011/013483 A1 | 2/2011 |

OTHER PUBLICATIONS

International Search Report and Written Opinion of PCT/2014/012448 mailed on Feb. 19, 2014, 8 pages.

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

European Search report Issued in European Patent Application No. 10/748,702.7, mailed Apr. 2, 2013.

Extended European Search Report issued in European Patent Application No. EP 10748677.1, mailed Nov. 19, 2012.

International Search Report (PCT/ISA/210) issued on Jul. 14, 2009, by Japanese Patent Office as the International Searching Authority for International Application No. PCT/JP2009/061318.

International Search Report and Written Opinion issued in PCT/JP2011/050925, mailed Apr. 12, 2011.

International Search Report and Written Opinion issued in PCT/JP2011/054134, mailed Apr. 12, 2011.

International Search Report and Written Opinion issued in PCT/JP2011/064768, mailed Sep. 13, 2011.

International Search Report and Written Opinion issued in PCT/JP2011/070450, mailed Dec. 13, 2011.

Kosaka, et al.,"Operating Point Control System for a Continuous Flow Artificial Heart: In Vitro Study," ASAIO Journal 2003, 6 pages.

Supplementary European Search Report issued in European Application No. 09/831,788.6, dated Jan. 7, 2013, 7 pages.

Terumo Heart, Inc., "Handled With Care—Significantly Reduce the Risk of Cell Damage," Terumo brochure, Apr. 2010, 2 pages.

Yamazaki, et al., "Development of a Miniature Intraventricular Axial Flow Blood Pump," ASAIO Journal, 1993, 7 pages.

International Search Report and Written Opinion mailed on May 14, 2014 for International Patent Application No. PCT/US2014/012511 filed on Jan. 22, 2014, all pages.

International Preliminary Report on Patentability mailed on Aug. 6, 2015 for International Patent Application No. PCT/US2014/012511 filed on Jan. 22, 2014, all pages.

\* cited by examiner

IMPELLER POSITION COMPENSATION USING FIELD ORIENTED CONTROL

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to centrifugal pumping devices for circulatory assist and other uses, and, more specifically, to an improved method and apparatus for maintaining a centered position of a magnetically-levitated impeller.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. The impeller can act as a rotor of an electric motor in which a rotating magnetic field from a multiphase stator couples with the impeller and is rotated at a speed appropriate to obtain the desired blood flow through the pump.

A typical cardiac assist system includes a pumping unit, drive electronics, microprocessor control unit, and an energy source such as rechargeable batteries and/or an AC power conditioning circuit. The system is implanted during a surgical procedure in which a centrifugal pump is placed in the patient's chest. An inflow conduit is pierced into the left ventricle to supply blood to the pump. One end of an outflow conduit is mechanically fitted to the pump outlet and the other end is surgically attached to the patient's aorta by anastomosis. A percutaneous cable connects to the pump, exits the patient through an incision, and connects to the external control unit.

A control system for varying pump speed to achieve a target blood flow based on physiologic conditions is shown in U.S. Pat. No. 7,160,243, issued Jan. 9, 2007, which is incorporated herein by reference in its entirety. A target blood flow rate may be established based on the patient's heart rate so that the physiologic demand is met. The control unit may establish a speed setpoint for the pump motor to achieve the target flow.

A typical centrifugal pump employs a design which optimizes the shapes of the pumping chamber and the impeller rotating within the chamber so that the pump operates with a high efficiency. By employing a magnetic bearing (i.e., levitation), contactless rotation of the impeller is obtained and the pumping chamber can be more completely isolated from the exterior of the pump. The impeller typically employs upper and lower plates having magnetic materials (the terminology of upper and lower being arbitrary since the pump can be operated in any orientation). A stationary magnetic field from the upper side of the pump housing attracts the upper plate and a rotating magnetic field from the lower side of the pump housing attracts the lower plate. The forces cooperate so that the impeller rotates at a levitated position within the pumping chamber. Features (not shown) may also be formed in the walls of the pumping chamber to produce a hydrodynamic bearing wherein forces from the circulating fluid also tend to center the impeller. Hydrodynamic pressure grooves adapted to provide such a hydrodynamic bearing are shown in U.S. Pat. No. 7,470,246, issued Dec. 30, 2008, titled "Centrifugal Blood Pump Apparatus," which is incorporated herein by reference.

The impeller has an optimal centered location within the pumping chamber with a predetermined spacing from the chamber walls on each side. Maintaining a proper spacing limits the shear stress and the flow stasis of the pump. A high shear stress can cause hemolysis of the blood (i.e., damage to cells). Flow stasis can cause thrombosis (i.e., blood clotting). In order to ensure proper positioning, active monitoring and control of the impeller position has been employed by adjusting the stationary magnetic field. However, position sensors and an adjustable magnetic source occupy a significant amount of space and add to the complexity of a system. With an implanted system, it is desirable to miniaturize the pump as much as possible. It is also desirable to reduce failure modes by avoiding complexity. Thus, it would be desirable to maintain a centered position of the impeller to limit hemolysis and thrombosis without needing active control of the stationary levitating magnetic field.

SUMMARY OF THE INVENTION

In one aspect of the invention, a centrifugal pump system comprises a disc-shaped impeller rotating about an axis and having a first magnetic structure disposed at a first surface and a second magnetic structure disposed at a second surface. A pump housing defines a pumping chamber which receives the impeller. A levitation magnetic structure is disposed at a first end of the pump housing having a levitating magnetic field for axially attracting the first magnetic structure. A multiphase magnetic stator disposed at a second end of the pump housing for generating a rotating magnetic field for axially and rotationally attracting the second magnetic structure. A commutator circuit provides a plurality of phase voltages to the stator. A sensing circuit determines respective phase currents flowing in response to the phase voltages. A controller calculates successive commanded values for the phase voltages in response to the determined phase currents and a variable commutation angle. The angle is selected to correspond to an axial attractive force of the stator that maintains a levitation of the impeller at a centered position within the pumping chamber.

DETAILED DESCRIPTION OF PREFERRED EMBODIMENTS

Figure 1:
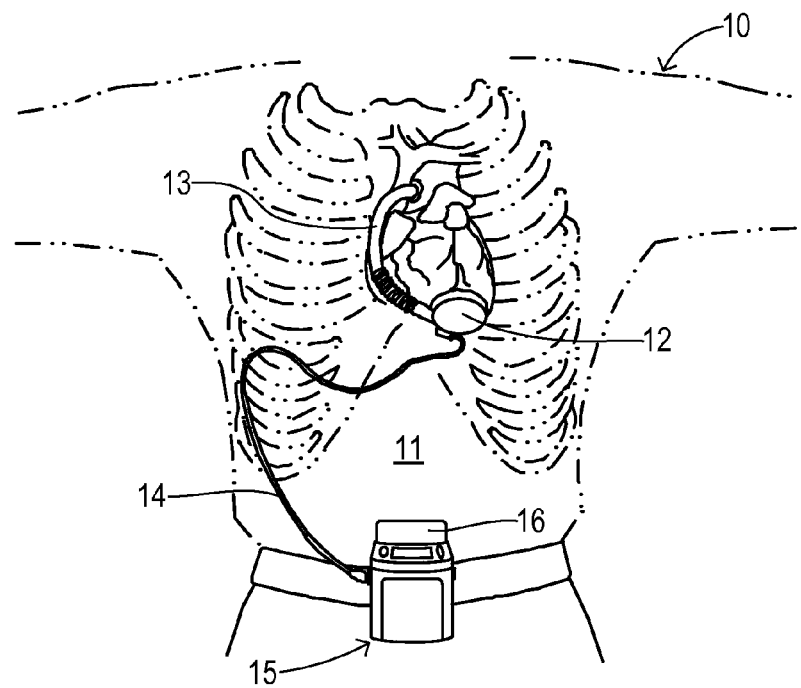
FIG. 1 is a diagram of a circulatory assist system as one example of an implantable pump employing the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's aorta. A percutaneous power cable 14 extends from pumping unit 12 outwardly of the patient's body via an incision to a compact control unit 15 worn by patient 10. Control unit 15 is powered by a main battery pack 16 and/or an external AC power supply and an internal backup battery. Control unit 15 includes a commutator circuit for driving a motor within pumping unit 12.

Figure 2:
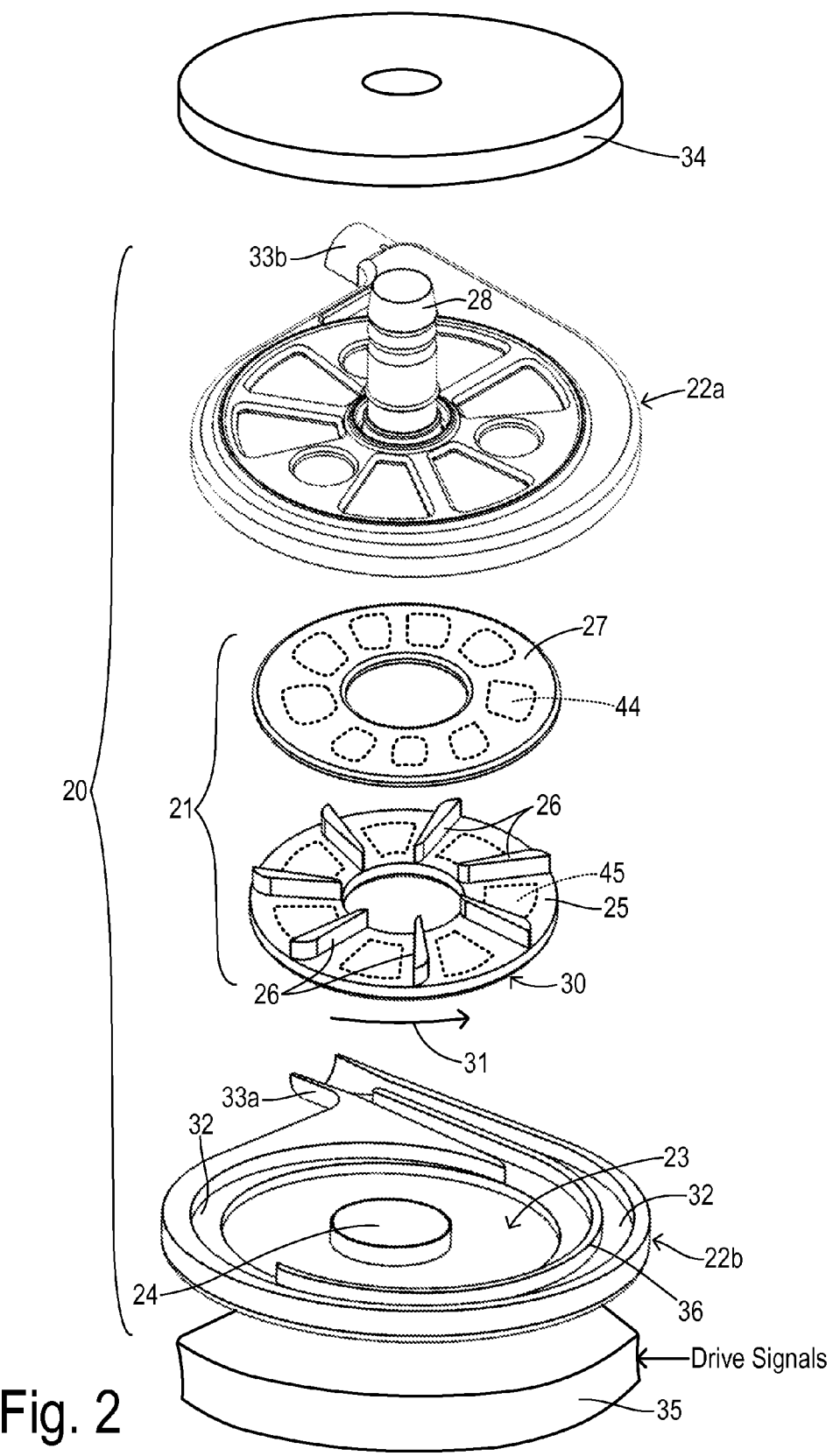
FIG. 2 is an exploded, perspective view of a centrifugal pump.

FIG. 2 shows a centrifugal pump unit 20 having an impeller 21 and a pump housing having upper and lower halves 22a and 22b. Impeller 21 is disposed within a pumping chamber 23 over a hub 24. Impeller 21 includes a first plate or disc 25 and a second plate or disc 27 sandwiched over a plurality of vanes 26. Second disc 27 includes a plurality of embedded magnet segments 44 for interacting with a levitating magnetic field created by levitation magnet structure 34 disposed against housing 22a. For achieving a small size, magnet structure 34 preferably is comprised of one or more permanent magnet segments providing a symmetrical, static levitation magnetic field around a 360° circumference. First disc 25 also contains embedded magnet segments 45 for magnetically coupling with a magnetic field from a stator assembly 35 disposed against housing 22b. Housing 22a includes an inlet 28 for receiving blood from a patient's ventricle and distributing it to vanes 26. Impeller 21 is preferably circular and has an outer circumferential edge 30. By rotatably driving impeller 21 in a pumping direction 31, the blood received at an inner edge of impeller 21 is carried to outer circumferential 30 and enters a volute region 32 within pumping chamber 23 at an increased pressure. The pressurized blood flows out from an outlet 33 formed by housing features 33a and 33b. A flow-dividing guide wall 36 may be provided within volute region 32 to help stabilize the overall flow and the forces acting on impeller 21.

Figure 3:
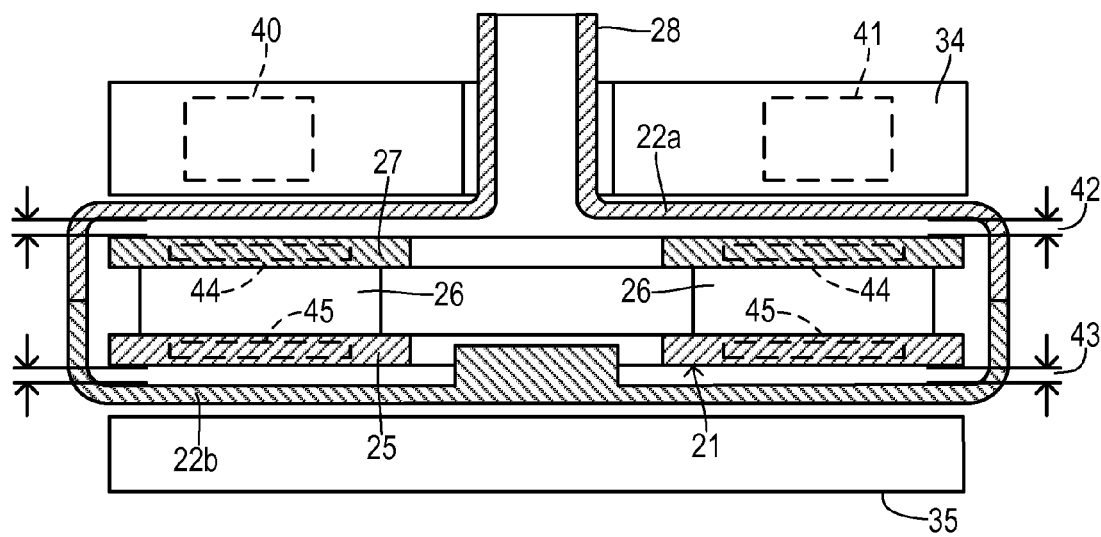
FIG. 3 is a cross section showing an impeller levitated to a centered position within a pumping chamber.

The cross section of FIG. 3 shows impeller 21 located at a centered position wherein disc 27 is spaced from housing 22A by a gap 42 and impeller disc 25 is spaced from housing 22B by a gap 43. During pump operation, the center position is maintained by the interaction of attractive magnetic forces between permanent magnets 40 and 41 in levitation magnet structure 34 with imbedded magnetic material 44 within impeller disc 27, and between stator assembly 35 and imbedded magnet material 45 in impeller disc 25, and by hydrodynamic bearing forces exerted by the circulating fluid which may be increased by forming hydrodynamic pressure grooves in housing 22 (not shown). By using permanent magnets in structure 34, a compact shape is realized and potential failures associated with the complexities of implementing active levitation magnet control are avoided. In order to properly balance impeller 21 at the centered position, however, and because other forces acting on impeller 21 are not constant, an active positioning control is still needed. In particular, the hydrodynamic forces acting on impeller 21 vary according to the rotational speed of impeller 21. Furthermore, the attractive force applied to impeller 21 by stator assembly 35 depends on the magnitude of the magnetic field and the angle by which the magnetic field leads the impellers magnetic field position.

A typical method for controlling voltages applied to a stator in order to provide the desired rotation for a permanent magnet rotor (i.e., the impeller) is a field-oriented control (FOC) algorithm, which is also known as vector control. It is known in FOC that the stator magnetic field should lead the impeller position by 90° for maximum torque efficiency. The magnitude of the attractive force on the impeller is proportional to the magnitude of the phase currents in the stator. Phase current is adjusted by the FOC algorithm according to torque demands for the pump. Since the commutation angle is typically fixed at 90°, the resulting attractive force varies according to torque output from the pump.

The present invention varies the commutation angle in a manner to compensate for variations in attractive force that would otherwise occur as a result of changes in speed and torque. Varying the commutation angle from 90° slightly reduces overall efficiency, but has no significant affect on overall pump performance. At any particular combination of the 1) magnitude of the phase current and 2) the speed of the impeller, a modified commutation angle for generating the phase voltages applied to the stator can be determined so that the attractive force generated by the stator properly balances they hydrodynamic forces and the magnetic forces of the levitation magnets in order to keep the impeller at the centered position.

Figure 4:
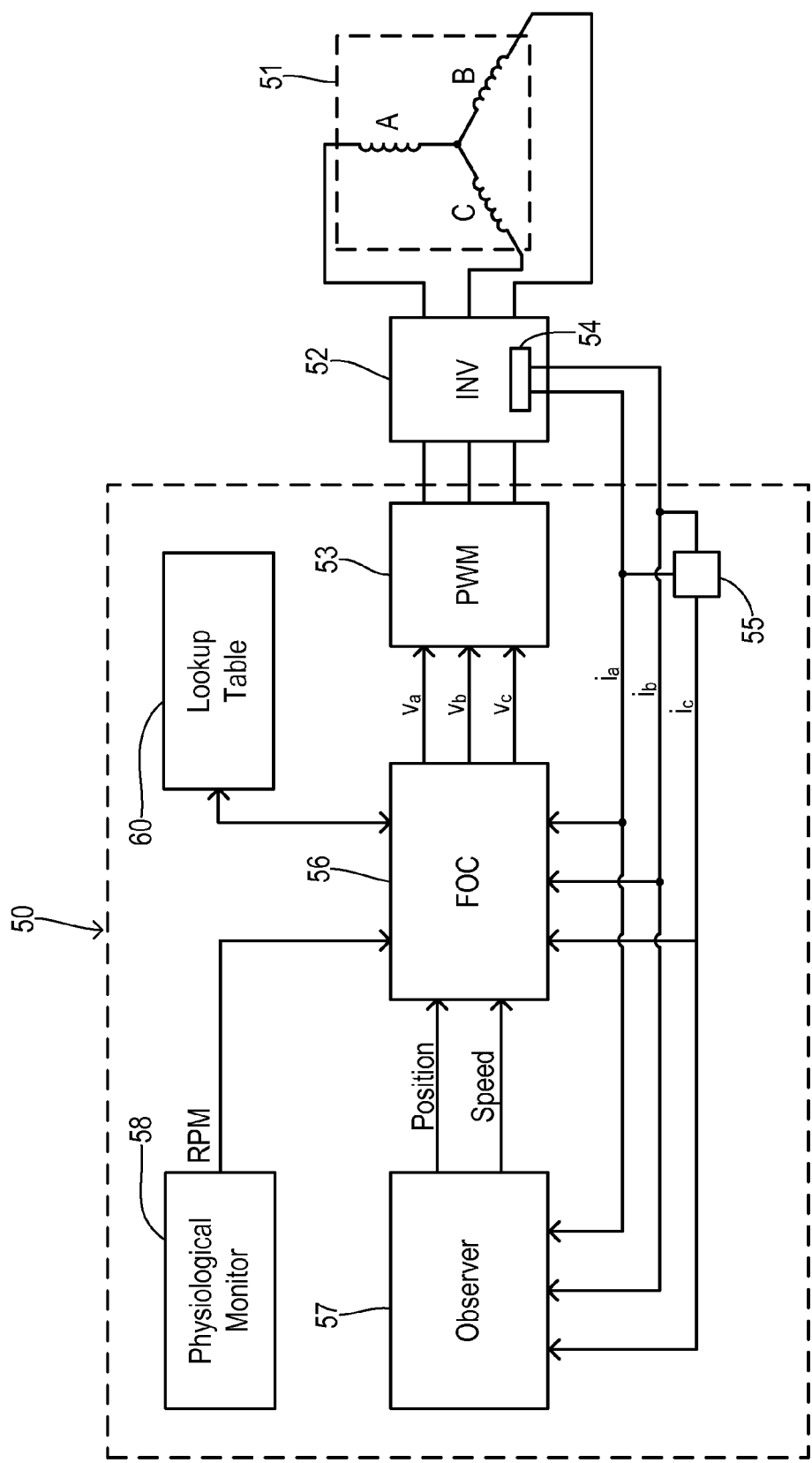
FIG. 4 is a block diagram showing multiphase stator windings and a control system according to the present invention.

The present invention is shown in greater detail in FIG. 4 wherein a controller 50 uses field oriented control to supply a multiphase voltage signal to a stator assembly 51 shown as a three-phase stator. Individual phases A, B, and C are driven by an H-bridge inverter 52 functioning as a commutation circuit driven by a pulse width modulator (PWM) circuit 53 in controller 50. A current sensing circuit 54 associated with inverter 52 measures instantaneous phase current in at least two phases providing current signals designated $i_a$ and $i_b$. A current calculating block 55 receives the two measured currents and calculates a current $i_c$ corresponding to the third phase as known in the art. The measured currents are input to an FOC block 56 and to a current observer block 57 which estimates the position and speed of the impeller as known in the art. The impeller position and speed are input to FOC block 56. A target speed or rpm for operating the pump is provided by a conventional physiological monitor 58 to FOC block 56. The target rpm may be set by a medical caregiver or determined according to an algorithm based on various patient parameters such heart beat.

FOC block 56 generates commanded voltage output values $v_a$, $v_b$, and $v_c$ which are input to PWM block 53. The $v_a$, $v_b$, and $v_c$ commands may also be coupled to observer 57 for use in detecting speed and position (not shown). The system in FIG. 4 generally uses conventional elements as known in the art except for modifications to FOC block 56 which alter the field oriented control algorithm so that a variable commutation angle is provided instead of the conventional 90° angle. In a preferred embodiment, a predetermined lookup table 60 is used to generate a commutation angle to be used at various operating conditions of the pump.

Figure 5:
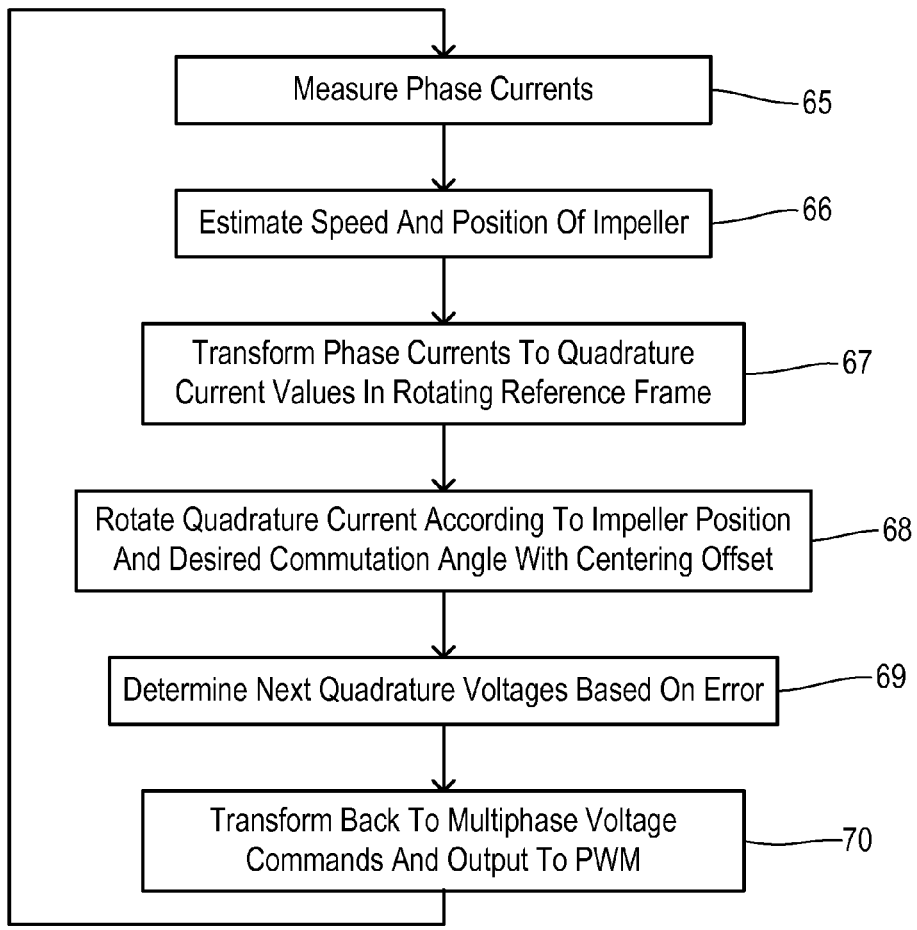
FIG. 5 is a flow chart showing one preferred method for controlling pump operation.

In a preferred embodiment, the invention proceeds according to a method as shown in FIG. 5 which highlights a portion of the field oriented control algorithm where a variable commutation angle is adopted. Thus, in step 65 the phase currents are measured. Based on the measured phase currents, the speed and position of the impeller are estimated in step 66. The phase currents are transformed into a two-axis coordinate system to generate quadrature current values in a rotating reference frame in step 67. In step 68, the quadrature current vector is rotated by a desired commutation angle. This angle is selected to provide a proper centering offset from the typical 90° commutation angle according to the phase current and speed as described below. Based on the difference (i.e., error) between the quadrature current values from steps 67 and 68, the next quadrature voltages are determined in step 69. In step 70, the quadrature voltages are transformed back to the stationary reference frame in order to provide the multiphase voltage commands which are output to the PWM circuit.

According to one preferred embodiment of the invention, the values for the commutation angle which are offset from 90° by a centering offset to properly balance the levitated position of the impeller are determined in advance for various operating conditions of the pump and are compiled into a lookup table for use during normal pump operation. The attractive force applied to the impeller by the stator assembly varies with the magnitude of the magnetic field and the angle by which the magnetic field leads the impeller position (i.e., the commutation angle). The magnitude of the magnetic field is directly proportional to the phase current. Phase current may preferably be characterized as the peak value for one of the measured phase currents over a sampling interval. In one preferred embodiment, a sampling interval of 1/20 seconds is used. Since the drive currents are always symmetrical, all the phases are driven with the same phase current value so that any one of the phase currents can be used. The phase current values are determined by the FOC algorithm according to the torque requirements of the motor in order to maintain the desired speed. Therefore, the phase currents cannot be used as the primary variable to adjust the axial attractive force. However, commutation angle can be arbitrarily modified to achieve a desired attractive force without otherwise degrading operation of the pump (although a slight reduction in efficiency is produced).

Figure 6:
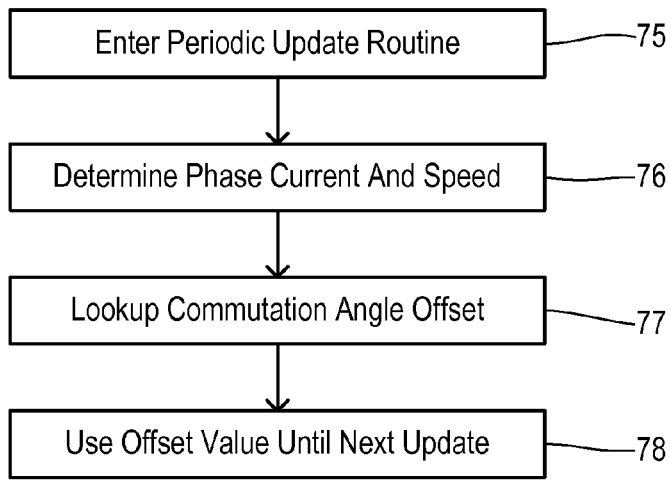
FIG. 6 is a flow chart showing one preferred method for adjusting a commutation angle.

Entries in the lookup table to be used to determine an offset commutation angle based on the magnitude of the phase current and the current operating speed, can be obtained experimentally during the design of the centrifugal pump system. During normal pump operation, a value for the commutation angle is obtained from the lookup table during each sampling interval using a method shown in FIG. 6. Thus, an update routine is periodically entered in step 75 according to the sampling interval. A phase current and speed characterizing the sampling interval are determined in step 76. In addition to peak current in a single phase, a phase current characteristic such as an RMS value or an average of the square of the current could be employed. Based on the phase current characteristic and the rotational speed of the impeller, an offset commutation angle is looked up in step 77. The offset can be stored as an absolute commutation angle or can be stored as a difference from a 90° commutation angle. The commutation angle offset is then used in step 78 for performing the field oriented control method of determining the phase voltages for driving the stator assembly until a next update for the following sampling interval.

In one preferred embodiment, the lookup table includes 16 rows corresponding to the phase current characteristic and 10 columns corresponding to speed. Each row or column covers a respective range of values and all the columns and rows together cover a full operating regime of the pump. The table values can be determined experimentally using an impeller attached to a torque meter. An attractive force measurement fixture is attached to the stator assembly. For each rpm range corresponding to a table column, the phase current characteristic (i.e., the torque) is set to a corresponding range for a table row, with the pump operating using a standard field oriented control algorithm. The commutation angle is manually adjusted while monitoring the change in attractive force until the desired attractive force is obtained. The commutation angle achieving the desired attractive force is then stored in the table.

The present invention is also useful in the context of a centrifugal pump with a levitating impeller wherein the impeller position can be sensed. Instead of a lookup table, a control loop varying the commutation angle could be employed in order to maintain the desired impeller position.

What is claimed is:

1. A centrifugal pump system comprising:
   a disc-shaped impeller rotating about an axis and having a first magnetic structure disposed at a first surface and a second magnetic structure disposed at a second surface;
   a pump housing defining a pumping chamber which receives the impeller;
   a levitation magnetic structure disposed at a first end of the pump housing having a levitating magnetic field for axially attracting the first magnetic structure;
   a multiphase magnetic stator disposed at a second end of the pump housing for generating a rotating magnetic field for axially and rotationally attracting the second magnetic structure;
   a commutator circuit for providing a plurality of phase voltages to the stator;
   a sensing circuit determining respective phase currents flowing in response to the phase voltages; and
   a controller configured to:
      calculate successive commanded values for the phase voltages in response to the determined phase currents; and
      select a variable commutation angle, wherein the angle is selected to correspond to an axial attractive force of the stator that maintains a levitation of the impeller at a centered position within the pumping chamber.

2. The system of claim 1 wherein the levitating magnetic field is substantially constant.

3. The system of claim 2 wherein the levitation magnetic structure is comprised of a permanent magnet material.

4. The system of claim 1 wherein the angle for calculating the commanded values is determined in response to a phase current characteristic and a rotational speed of the impeller.

5. The system of claim 4 wherein the phase current characteristic is comprised of a peak current flowing in the stator during a predetermined sampling interval.

6. The system of claim 4 wherein the controller includes a lookup table storing predetermined values for the commutation angle corresponding to respective ranges of the phase current characteristic and the rotational speed.

* * * * *